United States Patent [19]

Böhner et al.

[11] 4,226,614
[45] Oct. 7, 1980

[54] CYANOMETHYL ESTER OF 4-(P-TRIFLUOROMETHYLPHENOXY)-α-PHENOXYPROPIONIC ACID AND A METHOD OF CONTROLLING WEEDS THEREWITH

[75] Inventors: Beat Böhner, Binningen; Otto Rohr, Therwil, both of Switzerland

[73] Assignee: Ciba-Geigy Corporation, Ardsley, N.Y.

[21] Appl. No.: 8,624

[22] Filed: Feb. 1, 1979

[30] Foreign Application Priority Data

Feb. 3, 1978 [CH] Switzerland ............... 1214/78

[51] Int. Cl.² ............... A01N 9/20; C07I 121/75
[52] U.S. Cl. ............... 71/105; 260/465 D; 260/465.4
[58] Field of Search ............... 260/465 D; 71/105

[56] References Cited

U.S. PATENT DOCUMENTS 4,071,178  1/1978  Johnson et al. ............... 71/105

FOREIGN PATENT DOCUMENTS 856101  12/1977  Belgium .

Primary Examiner—Dolph H. Torrence
Attorney, Agent, or Firm—Harry Falber

[57] ABSTRACT

The present invention provides a novel herbicidally active ester, namely the cyanomethyl ester of 4-(p-trifluoromethylphenoxy)-α-phenoxypropionic acid of the formula

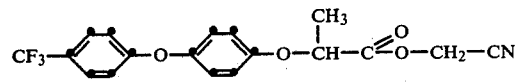

It is a further object of the invention to provide a herbicidal composition which contains this novel ester as active component and also a post-emergence method of selectively controlling monocotyledonous weeds in crops of dicotyledonous plants. The invention furthermore provides a process for the manufacture of the novel ester by methods which are known per se by reaction of a corresponding trifluoromethyl-phenoxy-α-phenoxypropionic acid halide with hydroxyacetonitrile (cyanomethanol) or by reaction of 4-(p-trifluoromethylphenoxy)-phenol with a α-halopropionic acid cyanomethyl ester.

2 Claims, No Drawings

CYANOMETHYL ESTER OF 4-(P-TRIFLUOROMETHYLPHENOXY)-α-PHENOXYPROPIONIC ACID AND A METHOD OF CONTROLLING WEEDS THEREWITH

The present invention relates to a novel herbicidally active ester, namely the cyanomethyl ester of 4-(p-trifluoromethylphenoxy)-α-phenoxypropionic acid, processes for the manufacture thereof, herbicidal compositions which contain said ester as active component, and a method of selectively controlling grass-like weeds in crops of dicotyledonous cultivated plants which comprises the use of the novel compound and compositions containing it.

Herbicidally active halogenated and/or trifluoromethylated cyanodiphenyl ethers and cyanoalkoxy diphenyl ethers have already been disclosed in German Offenlegungsschriften Nos. 1,912,600, 2,311,638, 2,613,675, 2,613,697 and 2,639,796 and also in U.S. Pat. Nos. 3,322,525 and 4,059,435. The cyanoethyl esters of 4-(p-trifluoromethylphenoxy)-α-phenoxypropionic acid have been described in Belgian Pat. No. 856,101 and German Offenlegungsschrift No. 2,628,384.

At low rates of application, the above compounds have a relatively weak action against grass-like (monocotyledonous) weeds in pre-emergence or post-emergence application or they are not selective in crops of dicotyledonous cultivated plants. Consequently, their suitability for the selective control of grass-like weeds in crops of dicotyledonous cultivated plants is limited.

Surprisingly, it has now been found that the cyanomethyl ester of 4-(p-trifluoromethylphenoxy)-α-phenoxypropionic acid has a much better action against grasses (monocots) and causes virtually no damage to crops of dicots, and is thus very suitable for controlling grass-like weeds in crops of dicotyledonous cultivated plants, such as cotton, soya bean, sugar beet, leguminosae etc. It is especially surprising that the novel ester of the invention is also distinctly superior to the corresponding cyanoethyl ester of German Offenlegungsschrift No. 2,628,384 in the control of resistant grass-like weeds (Avena fatua).

The novel ester of the present invention has the formula

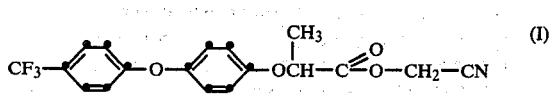 (I)

It is prepared by methods which are known per se.

In a first process, a 4-(p-trifluoromethylphenoxy)-α-phenoxypropionic acid halide of the formula II

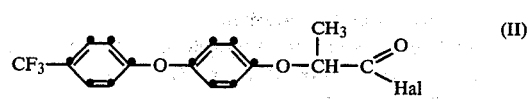 (II)

wherein Hal represents chlorine or bromine, is reacted in the presence of a basic acid acceptor, with cyanomethanol (hydroxyacetonitrile)

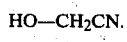
HO—CH$_2$CN.

In another process, the hydroxydiphenyl ether, or a salt thereof, of the formula III

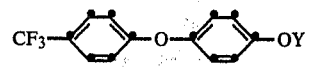 (III)

wherein Y represents hydrogen or the cation of an alkali metal, is reacted with an α-halopropionic acid cyanomethyl ester of the formula IV

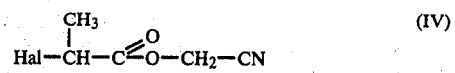 (IV)

wherein Hal represents chlorine or bromine, in the presence of an acid acceptor.

The starting materials of the formulae II and III are known. The compounds of the formula IV can be prepared in accordance with Example 2(a).

The reactions are preferably carried out in a solvent which is inert to the reactants. Suitable solvents are those of the most widely different classes, such as aliphatic and aromatic, unsubstituted or chlorinated hydrocarbons, and also polar inert organic solvents, such as ethers, ketones, amides, stable esters, for example methylene chloride, methyl ethyl ketone, dimethoxy ethane, dimethyl formamide, dimethyl sulfoxide, tetrahydrofurane etc.

Suitable basic acid acceptors for the reaction with the halogen compounds of the formula II and IV can be aqueous alkali metal hydroxides, such as KOH and NaOH, as well as further conventional bases, such as carbonates (K$_2$CO$_3$), alcoholates (NaOCH$_3$ and potassium tertbutylate), and organic bases, such as triethylamine etc.

The following Examples illustrate the manufacture of the novel ester of the formula I.

EXAMPLE 1

17.2 g (0.05 mole) of 4-(4'-trifluoromethylphenoxy)-α-phenoxypropionyl chloride are added dropwise at 10° C. to a mixture of 3.13 g (0.055 mole) of 100% hydroxyacetonitrile (cyanomethanol) and 5.5 g (0.54 mole) of triethylamine in 50 ml of methylene chloride. The reaction mixture is then stirred for 1 hour at room temperature. Then 100 ml of water are added and the organic phase is separated, filtered over a small column of silica gel and concentrated. The residual solid is triturated with petroleum ether, collected by filtration and dried, affording 13.2 g (72.5% of theory) of 4-(4'-trifluoromethylphenoxy)-α-phenoxy-propionic acid cyanomethyl ester with a melting point of 53°–56° C.

EXAMPLE 2

(a) 215.9 g (1 mole) of α-bromopropionyl bromide are dissolved in 500 ml of dimethoxy ethane and to the resulting solution are slowly added 62.8 g (1.1 moles) of cyanomethanol at 10° C. Then 111.3 g (1.1 moles) of triethylamine are added dropwise at 10°–20° C. The reaction mixture is stirred for 10 minutes at room temperature and filtered over hyflo. The filtrate is concentrated and the residue is distilled in a water jet vacuum, yielding as main fraction 107 g (55.7%) of α-bromopropionic acid cyanomethyl ester with a boiling point of 109° C./17 torr and having the formula

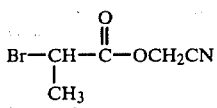

(b) 15.2 g (0.06 mole) of 4-(4'-trifluoromethylphenoxy)phenol and 9.7 g (0.07 mole) of potassum carbonate are stirred under reflux for 2 hours in 50 ml of methyl ethyl ketone. Then 12.1 g (0.063 mole) of the α-bromopropionic acid cyanomethyl ester obtained according to (a) are added and the reaction mixture is stirred for 15 hours at 50° C. The reaction mixture is filtered and concentrated. The residue is dissolved in methylene chloride and the solution is filtered over a small column of silica gel, concentrated and dried, affording 16.6 g (76%) of 4-(4'-trifluoromethylphenoxy)-α-phenoxy)-propionic acid cyanomethyl ester which is identical with the ester obtained according to Example 1 and which melts at 53°–56° C.

The compound (active substance) of the present invention is a stable compound which is soluble in conventional solvents, such as alkanols, ketones, ethers, dimethyl formamide, dimethyl sulfoxide etc.

The invention also relates to herbicidal compositions which contain the novel active substance of the formula I, and to a pre-emergence, especially post-emergence, method of controlling weeds, in particular monocotyledonous grass-like weeds.

The compositions of the present invention can be in the conventional formulations.

The compositions of the present invention are obtained in known manner by intimately mixing and grinding the active substance of the formula I with suitable carriers and/or adjuvants, with or without the addition of antiboams, wetting agents, dispersants or solvents which are inert to the active substance. The active substance can be processed to the following formulations:

solid formulations: dusts, tracking powders, granules (coated granules, impregnated granules and homogeneous granules);

active substance concentrates which are dispersible in water: wettable powders, pastes, emulsions, emulsifiable concentrates;

liquid formulations: solutions.

The above described compositions contain between 1 and 80% of active substance and can also be diluted before application to low concentrations, for example to about 0.05 to 1%. The rates of application are ordinarily 0.25 kg of active substance/ha, preferably between 0.25 and 4 kg/ha. The active substances can be formulated for example as follows (parts are by weight):

GRANULES

The following substances are used to formulate 5% granules:
- 5 parts of the ester of the formula I,
- 0.25 parts of epichlorohydrin,
- 0.25 parts of cetyl polyethyleneglycol ether with 8 moles of ethyleneoxide
- 3.50 parts of polyethylene glycol,
- 91 parts of kaolin (particle size 0.3–0.8 mm).

The active substance is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

WETTABLE POWDERS

The following constituents are used to formulate (a) a 50%, (b) a 25% and (c) a 10% wettable powder:
(a) 50 parts of the active substance of the formula I,
  5 parts of sodium dibutylnaphthylsulfonate,
  3 parts of naphthalenesulfonic acid/phenolsulfonic acid/formaldehyde concentrate (3:2:1),
  20 parts of kaolin,
  22 parts of Champagne chalk;
(b) 25 parts of the above active substance,
  5 parts of sodium oleylmethyltauride,
  2.5 parts of naphthalenesulfonic acid/formaldehyde condensate
  0.5 part of carboxymethyl cellulose,
  5 parts of neutral potassium aluminium silicate,
  62 parts of kaolin;
(c) 10 parts of the above active substance,
  3 parts of a mixture of the sodium salts of saturated fatty alcohol sulfates,
  5 parts of naphthalenesulfonic acid/formaldehyde condensate,
  82 parts of kaolin.

The indicated active substance is applied to the corresponding carriers (kaolin and chalk) and then these are mixed and ground, to yield wettable powders of excellent wettability and suspension powder. By diluting these wettable powders with water it is possible to obtain suspensions of the desired concentration of active substance. Such suspensions are used for controlling grass-like weeds in crops of cultivated plants.

PASTE

The following substances are used to formulate a 45% paste:
- 45 parts of active substance
- 5 parts of sodium aluminium silicate,
- 14 parts of cetyl polyethyleneglycol ether with 8 moles of ethylene oxide,
- 1 part of oleyl polyethyleneglycol ether with 5 moles of ethylene oxide,
- 2 parts of spindle oil,
- 10 parts of polyethylene glycol,
- 23 parts of water.

The active substance is homogeneously mixed with the adjuvants in appropriate devices and ground, yielding a paste from which, by dilution with water, it is possible to obtain suspensions of the desired concentration of active substance.

EMULSIFIABLE CONCENTRATE

The following ingredients are mixed to formulate a 25% emulsifiable concentrate:
- 25 parts of active substance
- 10 parts of a mixture of nonylphenolpolyoxy-ethylene and calcium dodecylbenzenesulfonate,
- 55 parts of xylene
- 10 parts of cyclohexanone.

This concentrate can be diluted with water to produce emulsions of suitable concentrations.

Compositions of the invention which contain, as active component, the novel ester of the formula I, are particularly suitable for the selective pre-emergence and, in particular, post-emergence control of monocotyledonous weeds in crops of dicotyledonous cultivated plants, for example soya bean, cotton, sugar beet, leguminosae, clover, alfalfa, melons, cucumbers, tobacco etc.

The following test methods were employed to establish the usefulness of the compound of the formula I as pre-emergence and post-emergence herbicide.

PRE-EMERGENCE HERBICIDAL ACTION

In a greenhouse, immediately after sowing the test plants in seed dishes, the surface of the soil is treated with an aqueous dispersion of the active substances, obtained from a 25% wettable powder or emulsifiable concentrate. Four different concentration series were used, corresponding to 4, 2, 1 and 0.5 kg of active substance per hectare respectively. The seed dishes are kept in the greenhouse at 22°–25° C. and 50–70% relative humidity. The test is evaluated 3 weeks later according to the following rating:

1 = plants have not germinated or are totally withered
2–3 = very strong action
4–6 = average action
7–8 = slight action
9 = no action (as untreated control)

The following test plants were used:
beta vulgaris (sugar beet)
glycine (soya)
gossypium (cotton)
avena fatua
lolium perenne
alopecurus myosuroides
bromos tectorum
cyperus esculentus
rottboellia exaltata
digitaria sanguinalis
setaria italica
echinochloa crus galli

POST-EMERGENCE HERBICIDAL ACTION (CONTACT HERBICIDE)

A large number of monocotyledonous weeds and dicotyledonous cultivated plants were sprayed after emergence in the 4- to 6-leaf stage with an aqueous active substance dispersion at rates of 0.125, 0.25, 0.5, 1 and 2 kg of active substance per hectare and kept at 24°–26° C. and 45–60% relative humidity. The test was evaluated, as in the pre-emergence test, 15 days after treatment in accordance with the same rating.

RESULTS OF THE POST-EMERGENCE TEST

| Plant | Concentration of active substance of the formula I kg/ha | | | | |
|---|---|---|---|---|---|
|  | 2 | 1 | 0.5 | 0.25 | 0.125 |
| Soya bean |  |  |  |  |  |
| (cultivated plant) | 9 | 9 | 9 | 9 | 9 |
| Lolium | 1 | 1 | 2 | 2 | 3 |
| Alopecurus | 1 | 1 | 1 | 2 | 2 |
| Bromus | 1 | 1 | 1 | 2 | 2 |
| Rottboellia | 1 | 1 | 1 | 1 | 1 |
| Digitaria | 1 | 1 | 1 | 1 | 1 |
| Setaria | 1 | 1 | 1 | 1 | 1 |
| Echinochloa | 1 | 1 | 1 | 1 | 1 |

In a comparison test, the selective herbicidal action of the cyanomethyl ester of the formula I in sugar beet with *Avena fatua* as weed was determined in a further post-emergence test and compared with the following structurally most closely related prior art compounds which contain cyano groups.

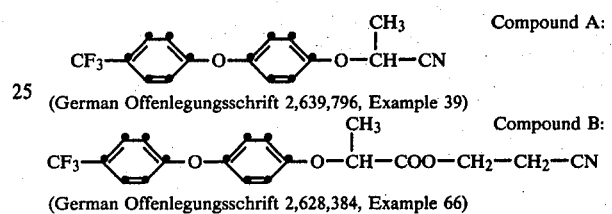

(German Offenlegungsschrift 2,639,796, Example 39)

$$CF_3-\text{⟨⟩}-O-\text{⟨⟩}-O-\overset{CH_3}{\underset{|}{C}H}-COO-CH_2-CH_2-CN \quad \text{Compound B:}$$

(German Offenlegungsschrift 2,628,384, Example 66)

The rate of application in this test was 0.125 kg/ha in each case. The test method and evaluation were identical with the preceding test.

Results

| Compound | Avena fatua | sugar beet |
|---|---|---|
| cyanomethyl ester of the formula I | 3 | 9 |
| A | 9 | 9 |
| B | 8 | 9 |

The above test shows clearly that the structurally most closely related compounds A and B virtually do not damage the monocotyledonous weed *Avena fatua* (wild oats) at all at the indicated application rate of 0.125 kg/ha, whereas the cyanomethyl ester of the invention severely damages the weed and is thus obviously superior to both comparison compounds in selective activity.

What is claimed is:

1. A method of selectively controlling *Avena fatua* in crops of dicotyledonous cultivated plants, which comprises post-emergence treatment of the *Avena fatua*-infested crops of cultivated plants with a herbicidally effective amount of the cyanomethyl ester of 4-(p-trifluoromethyl-phenoxy)-α-phenoxypropionic acid.

2. The method of claim 1, wherein said crop is sugar beets.